United States Patent [19]

Jung et al.

[11] Patent Number: 5,235,083
[45] Date of Patent: Aug. 10, 1993

[54] BIS(SILYL)ALKANES AND METHOD FOR THEIR PREPARATION

[75] Inventors: Il N. Jung, Seoul; Seung H. Yeon, Kyungki; Bong W. Lee, Kwangju, all of Rep. of Korea

[73] Assignee: Korea Institute of Science & Technology, Seoul, Rep. of Korea

[21] Appl. No.: 991,304

[22] Filed: Dec. 16, 1992

[30] Foreign Application Priority Data

Jan. 23, 1992 [KR] Rep. of Korea .................. 935/1992

[51] Int. Cl.$^5$ .............................................. C07F 7/08
[52] U.S. Cl. .................................................. 556/435
[58] Field of Search ........................................ 556/435

[56] References Cited

U.S. PATENT DOCUMENTS 5,075,477 12/1991 Jung et al. ......................... 556/435

OTHER PUBLICATIONS

"The Direct Synthesis of Organosilicon Compounds" by E. G. Rochow, J. American Chemical Society, 67, 963 (1945).
"Synthesis of Organosilicon Compounds. II. Comparative Activity of Various Types of Contact Masses Used for Synthesis of Methylchlorosilanes", Zhur. Obschei Khim., 27, 2475 (1957).
"Synthesis of Organosilicon Compounds. III. The Reaction of Direct Synthesis of Methylchlorosilanes", Zhur, Obschei Khim., 27, 2648 (1957).
"Catalyst Based on Copper Used in the Synthesis of the Methylchlorosilanes" by P. Trambouze et al., J. Chim. Phys., 51, 505 (1954).
"Mechanism and Kinetics of the Metal-Catalyzed Synthesis of Methylchlorosolanes. III. The Catalytically Active Form of the Copper Catalyst" by R. J. H. Voorhoeve et al., J. Catalysis, 4, 123 (1965).
"Organohalosilanes: Precursors to Silicones" by J. C. Vlugter et al., Conf. Accad. Lincei: Alta. Tech. Chim., 1961, p. 81 (1962).
"Formation of Organosilicon Compounds. 102." by G. Fritz et al., Z. Anorg. Allg. Chem., 512, 131 (1984).
"Synthesis of Organosilicon Compounds. XI. Formation of Silicon Methylene Compounds from Dichloromethane and Silicon", Z. Anorg. U. Allgem. Chem., 306, 39 (1960).

Primary Examiner—Paul F. Shaver
Attorney, Agent, or Firm—Birch, Stewart, Kolasch & Birch

[57] ABSTRACT

Bis(silyl)alkanes represented by the formulas (III), (IV) and (V)

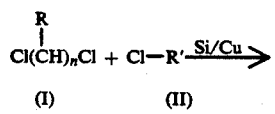

(I)     (II)

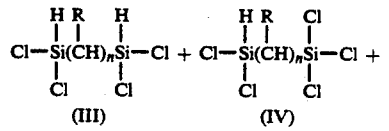

(III)        (IV)

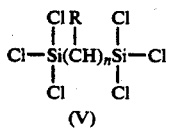

(V)

wherein R is H or phenyl, R' is a hydrogen atom or $C_{1-4}$ alkyl and n is an integer ranging from 1 to 4. The present invention also provides a method for preparation of the bis(silyl)alkanes comprising the steps of mixing an organic compound, which is represented by the formula (I) and has a chloro at each side of its molecule, with a hydrogen chloride or an organic chloride represented by the formula (II), the organic chloride being capable of generating the hydrogen chloride during its reaction, in order to provide a mixture and directly reacting this mixture with a metal silicon at a reaction temperature of 260° C.–370° C. in the presence of a copper catalyst.

16 Claims, No Drawings

BIS(SILYL)ALKANES AND METHOD FOR THEIR PREPARATION

BACKGROUND OF THE INVENTION

1. Field of the Invention

The present invention relates to bis(silyl)alkanes represented by the formulas (III), (IV) and (V), respectively, and a method for their preparation. In accordance with the present invention, in order to prepare the bis(silyl)alkanes represented by the formulas (III), (IV) and (V) at the same time, an organic chloride, represented by the formula (I) and having a chloro at each side of its molecule, is first mixed with a hydrogen chloride or an alkyl chloride represented by the formula (II), said alkyl chloride being capable of generating the hydrogen chloride during its reaction, in order to provide a mixture. This result mixture is in turn directly reacted with a metal silicon.

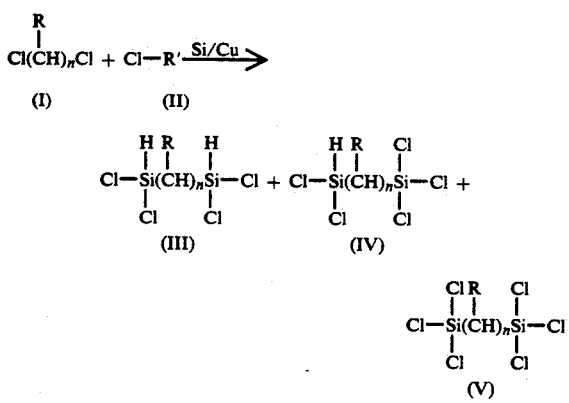

wherein R is H or a phenyl, R' is a hydrogen atom or a $C_{1-4}$ alkyl and n is an integer ranging from 1 to 4.

If described in detail, the present invention provides a novel and improved method for preparation of three types of bis(silyl)alkanes, the first being represented by the formula (III) and having two dichlorosilyls, the second being represented by the formula (V) and having two trichlorosilyls and the third being represented by the formula (IV) and having one dichlorosilyl and one trichlorosilyl, at the same time. In order to prepare these bis(silyl)alkanes, a gaseous mixture prepared by mixing the organic chloride of the formula (I), having a chloro at each side of its molecule, with the hydrogen chloride or the alkyl chloride of the formula (II), said alkyl chloride being capable of generating the hydrogen chloride during its reaction process, is directly reacted with the metal silicon in a fluidized-bed reactor or an agitation reactor at a reaction temperature of 260° C.-370° C. in the presence of copper catalyst. Such bis(silyl)alkanes having the chlorohydrosilyls have a property of easily further reacting with an organic compound having an unsaturated bond. In this regard, they can be used as effective starting materials for preparation of silicon compounds having several types of organic functional groups.

2. Description of the Prior Art

U.S. Pat. No. 2,380,995 discloses a known method for preparation of methylchlorosilanes, including dimethylchlorosilane, by direct reaction of a metal silicon with an organic halogen compound in the presence of a copper catalyst as represented by the reaction formula (VI) and this known method has been generally used as a basic technique recently in the silicon industry.

$$Si + 2CH_3Cl \xrightarrow{Cu} (CH_3)_2SiCl_2 \qquad (VI)$$

From the above direct reaction of the formula (VI), the desired reaction product, dimethylchlorosilane, together with other reaction products, such as methyltrichlorosilane, trimethylchlorosilane, tetrachlorosilane and etc., are prepared. This direct reaction is a complex reaction which also provides additional side products, such as small amount of material having a high boiling point, and in which change of the reaction conditions causes variation of the composition of the reaction products, including the desired reaction product. In this regard, it is necessary to accurately select the reaction condition, such as degree of purity of starting materials, kind and amount of catalyst, kind and amount of cocatalyst, reaction temperature, reaction pressure and type of reactor used, in order to efficiently prepare the desired reaction product, that is, the dimethylchlorosilane, using the above direct reaction represented by the formula (VI). In this direct reaction of a metal silicon with an organic chloride, it has been noted that the reaction can not be efficiently carried out if a catalyst, most preferably copper, is not used. In addition, a metal, such as zinc, aluminum or cadmium, may be used as a cocatalyst of this reaction, as required. This cocatalyst is used in order to not only reduce the reaction start time but also to improve selectivity of the dimethylchlorosilane of the reaction products, that is, the methylchlorosilanes [E. G. Rochow, J. Am. Chem. Soc., 67, 963 (1945)]. When the amount of the copper catalyst used in this direct reaction is increased, there is a problem in that the chlorine content of the reaction products is increased even though the reaction is accomplished in a short time. In this regard, it has been noted that it is good to use the copper catalyst of 10% by weight of the silicon in this direct reaction wherein the silicon is reacted with methyl chloride.

It has been reported that the copper, the catalyst of the reaction of the formula (VI), causes a silicon bond of the metal silicon to η-phase $Cu_3Si$ and this $Cu_3Si$ of the silicon bond is in turn reacted with the organic chloride [V. S. Fikhtengolts & A. L. Klebanskii, J. Gen. Chem. U.S.S.R., 27, 2535 (1957)]. In order to prepare the η-phase $Cu_3Si$, there has been proposed two types of preparation processes, that is, a physical process wherein both copper and silicon are heated to temperatures of 800° C.-1100° C. in the presence of inert gas [P. Trambouze, & B. Imelik, J. Chim. Phys., 51, 505 (1954)] and a chemical process wherein cuprous chloride is reacted with silicon as represented by the reaction formula (VII) [R. J. H. Voorhoeve. & J. C. Vlugter, J. Catalysis, 4, 129 (1965)].

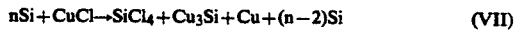

$$nSi + CuCl \rightarrow SiCl_4 + Cu_3Si + Cu + (n-2)Si \qquad (VII)$$

Conventionally, the reaction of the silicon with the methyl chloride is a high temperature reaction which is carried out at a high temperature not lower than 300° C. In addition, this reaction is an exothermic reaction. In this regard, the heat of this reaction not only causes the reactants to flocculate with each other but also introduces partial overheating if the excess heat if it is not efficiently removed [A. L. Klebamskii & V. S. Fikhtengolts, J. Gen. Chem. U.S.S.R., 27, 2693 (1957)]. Additionally, if the reaction temperature is higher than a predetermined proper temperature, this reaction results in reduction of the production amount of the desired dimethylchlorosilane as well as introduction of several side reactions. Such a high reaction temperature also causes the methyl chloride, the start material, and the reaction products to be decomposed and, as a result, carbons to be deposited on the silicon surfaces. As a result, silicon activity is rapidly deteriorated [J. C. Vlugter & R. J. H. Voorhoeve, Conf. Accad. Lincei, Alta Tech. Chim. 1961, p 81 (1962)]. In this regard, it is very important to control the reaction temperature in preparation of methylchlorosilanes in accordance with the direct reaction of the formula (VI).

In the direct reaction of the formula (VI), three types of reactors, otherwise stated, stationary type, agitation type and fluidized-bed type reactors are generally used. The agitation reactors have an advantage in that its temperature control is more easily carried out in comparison with the stationary reactor. It provides good reactivity since it causes the solid particles to collide with each other and, as a result, refresh their surfaces. Conventionally, since the copper catalyst of this reaction, has a density of three times of the silicon reactant of this reaction, it is very difficult to effectively mix the two materials with each other.

In order to overcome this problem, there has been proposed a method wherein the reaction is carried out under the condition that the solids at the bottom of the reactor are forced to move upwards by a spiral agitator and, at the same time, gaseous organic chloride is blown upwards [J. E. Sellers & J. L. Davis, U.S. Pat. No. 2,449,821]. However, this method requires reacting strong corrosive organic chloride with other reactants at a high temperature. In this respect, this method has a problem in that is necessarily requires a reactor having such excellent corrosion resistance that the reactor sufficiently resists the corrosive organic chloride. However, such a reactor can not be easily obtained. Furthermore, it is noted that this method is not proper for mass production of the desired reaction product and continuous reaction process.

In order to solve the above problems introduced by the known method such as disclosed in the above U.S. Pat. No. 2,449,821, several type of fluidized-bed reactors have been proposed such as disclosed in U.S. Pat. No. 2,887,502 of B. A. Bluestrin. In this fluidized-bed reactor, silicon and copper are reacted with each other under the condition that methyl chloride is blown upwards and, at the same time, the silicon and the copper are fluidized. This method using the fluidized-bed reactor efficiently removes the heat of reaction and, in this respect, is widely used in preparation of methylchlorosilanes.

Meanwhile, it is possible to prepare organic silicon compounds by directly reacting organic material, having at least two halogen atoms bonded thereto, with metal silicon. For example, U.S. Pat. Nos. 2,381,000, 2,381,001 and 2,381,002 disclose that a linear or cyclic chlorosilaalkane is prepared, as represented by the reaction formula (VIII), by reaction of methylene chloride with silicon in a fluidized-bed reactor. However, the prior art including the above U.S. Patents have not reported on accurate yield of the reaction products.

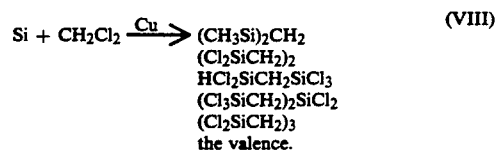

In reaction with the metal silicon, the methylene chloride can be reacted with the metal silicon at a relatively lower temperature in comparison with the methyl chloride. However, this reaction, wherein the methylene chloride is reacted with the metal chloride, results in dechlorination as well as dehydrochlorination at a high reaction temperature of about 300° C. since the methylene chloride has an excellent reactivity. In this respect, this reaction produces several types of reaction products. Thus in this reaction, the reactants are decomposed into chlorines and hydrogen chlorides simultaneously with generation of carbons. These carbons are deposited on the surfaces of silicons and this causes the activity of the silicons to be rapidly deteriorated.

G. Fritz et al. reported on that when the above reaction was carried out using a fluidized-bed type reactor at a reaction temperature of 320° C., the production amount of the reaction products having high molecular weight is increased [G. Fritz & A. Worsching, Z. Anorg. Allg. Chem., 512, 131 (1984)].

The aforementioned reaction generally produces five kinds of reaction products. Otherwise stated, this reaction produces bis(silyl)alkanes, which are compounds having two dichlorosilyls, two trichlorosilyls or one dichlorosilyl and one trichlorosilyl, a straight chain carbosilane such as 1,3,5-trisilapentane or 1,3,5,7-tetrasilaheptane, a cyclic carbosilane which is a compound having a long substituent at its silicon and a cyclic carbosilane which is a compound having a long substituent at its carbon. This reaction also produces a high-molecular compound similar to molasses or tar. However, it has been noted that no reaction product of the above products has yield higher than 30%, and furthermore, the maximum yield of a reaction product is about 20% at the most [G. Fritz & E. Tatern, "Carbosilanes-Syntheses and reactions", Spring-Verlag, New York, 1986]. G. Fritz et al. reported that in accordance with a reaction of methylene chloride with metal silicon, bis(-trichlorosilyl)(dichlorosilyl)alkane having Si—H bond was prepared in the form of side product of 3% [G. Fritz & H. Thielking, Z. Anorg. Allgem. Chem., 306, 39 (1960)].

The present inventors proposed that as represented by the reaction formula (VIIII), trisilaalkane as a reaction product and disilaalkane as a side product were prepared, using an agitation reactor having a spiral agitator or a fluidized-bed reactor, by a direct reaction of silanes having chloromethyl with silicon under the condition that the reaction temperature was controlled not to be higher than 350° C. and, at the same time, the copper catalyst is controlled in its using amount to be 10–15%. In addition, it was noted that the fluidity of the reactants together with the reactivity and selectivity of silicon is improved when spherical fine powder of acid white clay of 5-50% by weight of the silicon was added to the reaction in order to promote the fluidization of the reactants [Korean Patent Appln. No. 91-1055].

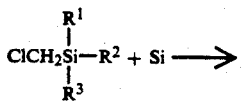

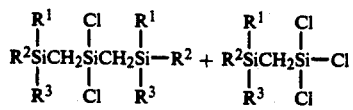

wherein $R^1$, $R^2$ and $R^3$ are a methyl or a chloro, respectively.

In addition, the present inventors proposed that as represented by the reaction formula (X), two kinds of bis(silyl)methanes were prepared when the compound represented by the formula (II) is used as a source of hydrogen chloride in a reaction of silanes having chloromethyl with metal silicon. The compound of the formula (II) is selected from, for example, 1,2-diethane chloride or hydrogen chloride, propyl chloride, n-butyl chloride and t-butyl chloride. In addition, it is preferred to use organic chlorides, such as hydrogen chlorides or butyl chlorides which are easily decomposed at the reaction temperature in order to generate hydrogen chloride [Korean Patent Appln. No. 91-24243].

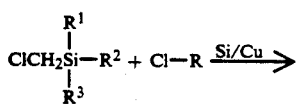

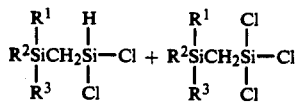

wherein $R^1$, $R^2$ and $R^3$ are a methyl or a chlorine, respectively, R is $C_{1-4}$ alkyl, H, Cl or $CH_2CH_2Cl$.

DETAILED DESCRIPTION OF THE INVENTION

The present invention provides a method for preparation of the bis(silyl)alkanes represented by the formulas (III), (IV) and (V), respectively. In order to prepare the bis(silyl)alkanes, a gaseous mixture, which is prepared by mixing an organic chloride represented by the formula (I) with a hydrogen chloride or an alkyl chloride represented by the formula (II), is directly reacted with a metal silicon. Here, the alkyl chloride is capable of generating the hydrogen chloride during its reaction.

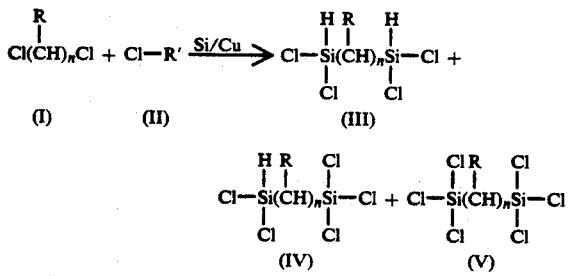

wherein R is H or phenyl, R' is a hydrogen atom or $C_{1-4}$ alkyl and n is an integer ranging from 1 to 4.

Described in detail, the present invention provides a novel method for preparing three kinds of bis(silyl)alkanes at the same time. These reaction products, bis(silyl)alkanes, that is, a bis(silyl)alkane having two dichlorosilyls and represented by the formula (III), a bis(silyl)alkane having two trichlorosilyls and represented by the formula (V) and a bis(silyl)alkane having one dichlorosilyl and one trichlorosilyl and represented by the formula (IV). In order to prepare the bis(silyl)alkanes, a gaseous mixture prepared by mixing the organic chloride of the formula (I), having a chloro at each side of its molecule, with the hydrogen chloride or the alkyl chloride of the formula (II), said alkyl chloride being capable of generating the hydrogen chloride during its reaction process, is directly reacted with the metal silicon in a fluidized-bed reactor or an agitation reactor at a reaction temperature of 260° C. -370° C. in the presence of a copper catalyst. Such bis(silyl)alkanes having the chlorohydrosilyls have a property of easily further reacting with an organic compound having an unsaturated bond and, in this regard, they can be used as effective starting materials for preparation of silicon compounds having several types of organic functional groups.

In order to prepare the gaseous mixture prior to its direct reaction with the metal silicon, gaseous organic compound of the formula (I) and gaseous hydrogen chloride or gaseous alkyl chloride of the formula (II) are mixed with each other. Otherwise, the compound of the formula (II) may be blown into liquid compound of the formula (I) in order to cause the compounds to mix with each other. Here, the mixing ratio of the mixture may be determined on the basis of weight % or volume % without limit. If the content of the compound of the formula (II) is increased, the production ratio of the bis(silyl)alkane of the formula (III) of the reaction products is increased. Hence, in order to increase the production ratio of the bis(silyl)alkane of the formula (III) having silicon-hydrogen bond, the compounds of the formulas (II) and (I) are preferred to be mixed with each other at a molar ratio of 0.1-6.0:1, preferably 2-2.5:1.

The reactor used in this invention is preferably selected from the agitation reactors and the fluidized-bed reactors which are suitable for a batch reaction and a continuous reaction. The metal silicon is selected from conventional industrial silicons having a degree of purity higher than 95%, preferably higher than 98%. The size of the silicon powder used in this reaction is preferred to be in the range from $1\mu$ to $200\mu$. However, the size distribution of the silicon powder may be changed in accordance with the size and type of the usedreactor. For example, when a fluidized-bed reactor is used, the size of the silicon powder is preferably in the range from $20\mu$ to $200\mu$. In addition, the reaction temperature is controlled to be 200° C.-350° C., preferably 250° C.-320° C. The reaction pressure is controlled to be range from atmospheric pressure (or 1 atm) to 5 atm. Here, the increase of the reaction pressure causes the reaction rate to be increased.

The catalyst used in this reaction is selected from a copper or a copper compound, said copper compound being capable of generating the copper under the given reaction condition. The amount of the copper catalyst is 1-20%, preferably 5-10%, by weight of the reactants. In addition, a cocatalyst of 0.001-2% by weight of the use copper catalyst may be applied to the reaction in order to cause both the reaction rate and selectivity of the desired reaction product to be improved. The cocatalyst of this invention is preferably selected from metals, such as calcium, zinc, lead, cadmium, manganese, magnesium, silver and chrome, and compounds thereof. However, the cocatalyst may be selected from other metals and compounds thereof. When the cocatalyst is added to the reaction, at least one of the aforementioned metals and compounds thereof is selected as the cocatalyst and its amount is 0.01-5% by weight of the solid reactants.

The following examples are merely intended to illustrate the present invention in further detail and should be no means be considered to limitative of the scope of the invention.

EXAMPLE 1

Preparation (I) of Si/Cu Contact Mixture 360 g of metal silicon (100-325 mesh) and 62.3 g of cuprous chloride (CuCl), a kind of copper catalyst, were added into a reactor which was in turn heated to a temperature of 250° C. The resulting mixture was then dried for about 2 hours in the presence of dried nitrogen gas. After the drying process was accomplished, the reactor was again heated to a temperature of 370° C. This caused silane tetrachloride to be prepared as a reaction product and, as a result, Si/Cu contact mixture, which was to be used in this invention and had a high activity, to be prepared. The reaction was carried out at the temperature of 370° C. in order to prepare the contact mixture. Thereafter, the silane tetrachloride was obtained. When a cocatalyst, such as cadmium, tin, zinc and etc., was used besides the copper catalyst, required amount of cocatalyst was added to the reactor through the opened lid of the reactor after the contact mixture was prepared and in turn agitated in order to be sufficiently mixed with the starting materials. This agitation was followed by the aforementioned reaction of the start materials.

EXAMPLE 2

Preparation (II) of Si/Cu Contact Mixtures 360 g of metal silicon (100-325 mesh) and 40 g of copper catalyst were added into the reactor and in turn dried under the same condition as that of Example 1. After the drying process was accomplished, the reactor was heated to a temperature of 350° C. and methyl chloride (CH$_3$Cl) was blown into the reactor through a preheated pipe, mounted on a lower part of the reactor. The reaction initially generated some water, and thereafter, started preparation of reaction products, that is, dimethyldichlorosilane and methyltrichlorosilane, when 40-70 minutes had elapsed. These reaction products were gathered by a gathering flask. The preparation of such reaction products proved that the Si/Cu contact mixture was prepared. This reaction of the methyl chloride with the reactants were carried out for about 2 hours. When 2 hours had elapsed, the addition of the methyl chloride was stopped and the reaction products gathered by the gathering flask were obtained. If it was required to add a cocatalyst to the reactants in the reactor, the cocatalyst was added to and reacted with the reactants in the same manner as that of the Example 1.

This reaction was repeated several times with change of both mixing ratios of the catalysts and the cocatalysts and this caused several types of Si/Cu contact mixtures, of which compositions are given in Table 1, to be prepared.

TABLE 1

[Compositions of Si/Cu contact mixtures to be used in this invention]

| Samp. Nos. | Metal Si (g) | Cu Catalyst kinds | (g) | Cocatalyst kinds | (g) | kinds | (g) |
|---|---|---|---|---|---|---|---|
| I-1 | 360 | CuCl | 62.3 | | | | |
| I-2 | 380 | Cu | 20.0 | | | | |
| I-3 | 360 | Cu | 40.0 | Cd | 2.0 | | |
| I-4 | 360 | Cu | 40.0 | Zn | 2.0 | | |
| I-5 | 380 | Cu | 20.0 | Cd | 2.0 | Sn | 0.02 |
| I-6 | 380 | Cu | 20.0 | Ca | 2.0 | | |
| I-7 | 380 | Cu | 20.0 | Ca | 2.0 | Cd | 2.0 |
| I-8 | 360 | Cu | 40.0 | Ag | 2.0 | | |
| I-9 | 360 | Cu | 40.0 | Ag | 2.0 | Cd | 2.0 |
| I-10 | 360 | Cu | 40.0 | Mn | 2.0 | | |
| I-11 | 360 | Cu | 40.0 | Mn | 2.0 | Cd | 2.0 |
| I-12 | 360 | Cu | 40.0 | Mg | 2.0 | | |
| I-13 | 360 | Cu | 40.0 | Mg | 2.0 | Cd | 2.0 |
| I-14 | 360 | Cu | 40.0 | Cr | 2.0 | | |
| I-15 | 360 | Cu | 40.0 | Cr | 2.0 | Cd | 2.0 |

EXAMPLES 3-1 to 3-5

Reactions of gaseous mixture of 1:3 mixing ratio of methylene chloride and hydrogen chloride with metal silicon The following description is concerned with Example No. 3-4 of Table 2. 402 g of Si/Cu contact mixture of Sample No. I-3 of Table 1 was added into the reactor which was in turn heated to a temperature of 320° C. Thereafter, nitrogen gas was blown into the reactor at a rate of 240 ml/min and, at the same time, hydrogen chloride was added into the reactor at a rate of 700 ml/min under the condition that methylene chloride was added into the reactor through an injection pump which was mounted on a lower part of the reactor. Here, the methylene chloride was added to the reactor at a rate of 0.667 ml/min. The reaction temperature rose due to exothermic reaction just after the reaction started and, at the same time, a reaction product was initially gathered by a gathering flask which was mounted on an upper part of the reactor. This reaction condition was maintained with no change and the reaction product of the gathering flask was collected at every 1 hour interval. When 4 hours of reaction time elapsed, 212.0 g of methylene chloride had been used while 321.6 g of reaction product had been prepared. This reaction product was in turn analyzed using a gas chromatograph (packed column, 5% SE-54, 0.9 m×⅛" O.D., SS, TCD.) Also in order to determine composition of the reaction product, this reaction product was fractionally distilled and determined in its composition using a conventional nuclear magnetic resonance spectrum. In accordance with the fractional distillation, the composition of the reaction product was determined to be 74.3 g (23.1%) of 1,1,3,3-tetrachloro-1,3-disilapropane [boiling point: 142°-143° C.; NMR (δ, CDCl$_3$) 5.70(t, 2H, Si-H), 1.39 (t, 2H, —CH$_2$—)], 101.3 g (31.5%) of 1,1,1,3,3-pentachloro-1,3-disilapropane [boiling point: 158°-159° C.; NMR (δ, CDCl$_3$) 5.75(t, 1H, Si-H), 1.63 (d, 2H, —CH$_2$)] and 27.0 g (8.4%) of 1,1,1,3,3,3-hexachloro-1,3-disilapropane [boiling point: 173°-174° C.; NMR (δ, CDCl$_3$) 1.74 (s, 2H, —CH$_2$)].

The balance (37.0%) was composed of 23.0% of trichlorosilane, 2% of tetrachlorosilane and the other materials which were unidentified.

The reaction was repeated several times under the same condition as that of Example 3-4 except for the reaction temperature. The results are given in Table 2.

I-15 of Table 1) for the contact mixture of Sample No. I-3 of Table 1. The results are given in Table 4.

TABLE 2

[Compositions of the reaction products of reactions of a gaseous mixture of methylene chloride and hydrogen chloride with metal silicon]

| Exam. Nos. | T. (°C.) | $CH_2Cl_2$ (g) | Reaction Time (hr) | Reaction product (g) | Compositions of Reation Products (%) | | | Balance |
|---|---|---|---|---|---|---|---|---|
| | | | | | Compound of formula (III) | Compound of formula (IV) | Compound of formula (V) | |
| 3-1 | 260 | 106.0 | 2.0 | 131.1 | 24.2 | 25.4 | 4.9 | 45.5 |
| 3-2 | 280 | 212.0 | 4.0 | 273.6 | 28.6 | 26.8 | 7.2 | 37.4 |
| 3-3 | 300 | 53.0 | 1.0 | 74.6 | 25.4 | 27.1 | 10.8 | 36.7 |
| 3-4 | 320 | 212.0 | 4.0 | 321.6 | 23.1 | 31.5 | 8.4 | 37.0 |
| 3-5 | 340 | 212.0 | 4.0 | 360.8 | 22.5 | 32.7 | 8.1 | 36.7 |

TABLE 4

[Compositions of the reaction products in accordance with compositions of catalysts]

| Exam. Nos. | Contact Mixtures | $CH_2Cl_2$ (g) | Reaction Time (hr) | Product (g) | Compositions of Products (%) | | | Balance |
|---|---|---|---|---|---|---|---|---|
| | | | | | Compound of formula (III) | Compound of formula (IV) | Compound of formula (V) | |
| 5-1 | I-1 | 280.0 | 5.3 | 547.2 | 12.8 | 37.4 | 4.4 | 45.4 |
| 5-2 | I-2 | 106.0 | 2.0 | 158.4 | 10.6 | 36.5 | 7.2 | 45.7 |
| 5-3 | I-4 | 280.0 | 5.3 | 523.2 | 4.2 | 41.8 | 8.8 | 45.9 |
| 5-4 | I-5 | 106.0 | 2.0 | 162.4 | 7.8 | 40.2 | 12.8 | 39.2 |
| 5-5 | I-6 | 106.0 | 2.0 | 153.6 | 10.8 | 32.4 | 18.4 | 38.4 |
| 5-6 | I-7 | 106.0 | 2.0 | 152.1 | 19.7 | 30.6 | 16.5 | 33.2 |
| 5-7 | I-8 | 106.0 | 2.0 | 161.3 | 14.2 | 24.3 | 19.3 | 42.2 |
| 5-8 | I-9 | 106.0 | 2.0 | 164.8 | 17.4 | 27.5 | 17.1 | 38.0 |
| 5-9 | I-10 | 106.0 | 2.0 | 151.0 | 11.5 | 32.4 | 6.7 | 43.6 |
| 5-10 | I-11 | 106.0 | 2.0 | 154.4 | 23.1 | 36.2 | 5.0 | 38.7 |
| 5-11 | I-12 | 106.0 | 2.0 | 152.8 | 13.2 | 36.2 | 6.2 | 44.4 |
| 5-12 | I-13 | 106.0 | 2.0 | 160.0 | 25.9 | 28.1 | 4.9 | 41.1 |
| 5-13 | I-14 | 106.0 | 2.0 | 156.0 | 13.6 | 33.2 | 9.7 | 43.5 |
| 5-14 | I-15 | 106.0 | 2.0 | 157.6 | 16.3 | 32.6 | 9.8 | 41.3 |

EXAMPLES 4-1 to 4-4

Reactions of a gaseous mixture of methylene chloride and hydrogen chloride with metal silicon The reactions of these Examples were carried out under the same condition [type of reactor, the contact mixture, reaction temperature (320° C.) and etc.] as that of Example 3 except for the molar ratio of the hydrogen chloride and methylene chloride. The results are given in Table 3. In Table 3, the Example No. 4-2 particularly showed the result of a reaction wherein 20.0 g (or 5% of amount of the contact mixture) of acid white clay was additionally added to the reactants.

TABLE 3

[Compositions of the reaction products in accordance with molar ratios of methylene chloride and hydrogen chloride]

| Exam. Nos. | $CH_2Cl_2$ (g) | Reaction Time (hr) | Molar ratio $CH_2Cl_2$ & HCl | Product (g) | Compositions of Reation Products (%) | | | Balance | Others |
|---|---|---|---|---|---|---|---|---|---|
| | | | | | Compound of formula (III) | Compound of formula (IV) | Compound of formula (V) | | |
| 4-1 | 106.0 | 2.0 | 1:2 | 142.6 | 18.3 | 36.5 | 14.4 | 30.8 | |
| 4-2 | 106.0 | 2.0 | 1:3 | 158.2 | 24.5 | 30.7 | 9.7 | 35.1 | 5% of White Clay Used |
| 4-3 | 106.0 | 2.0 | 1:4 | 172.6 | 21.4 | 28.6 | 5.7 | 44.3 | |
| 4-4 | 106.0 | 2.0 | 1:6 | 186.4 | 18.3 | 25.2 | 4.3 | 52.2 | |

EXAMPLES 5-1 to 5-14

Reactions of gaseous mixture of methylene chloride and hydrogen chloride with metal silicon Example 3-4 was repeated several times, substituting the contact mixtures (Sample Nos. I-1, I-2 and I-4 to EXAMPLES 6-1 to 6-3

Reactions of gaseous mixture of methylene chloride and alkyl chloride with metal silicon The following description is concerned with Example No. 6-1 of Table 5. The contact mixture of Sample No. I-3 of Table 1 was prepared, and thereafter, start materials, that is, 106.0 g (1.247 moles) of methylene chloride and 346.0 g (3.741 moles) of t-butyl chloride, were sufficiently mixed with each other in order to prepare a mixture of 1:3 molar ratio of the methylene chloride and the t-butyl chloride. This mixture was in turn added into the reactor at a rate of 113 ml/hr at a temperature of 320° C., and thereafter, reacted with the metal silicon for 4 hours. In result, 158.8 g of reaction product was prepared. In this reaction, it was observed that substantial amount of gas was not condensed on a condenser but escaped from the reactor. This gas was isobutane which was generated because of decomposition of t-butyl chloride at the high reaction temperature.

Table 5 shows compositions of reaction products prepared by reactions of the gaseous mixtures of methylene chloride and several types of alkyl chlorides with metal silicon.

TABLE 5

[Compositions of reaction products prepared by reactions of gaseous mixtures of methylene chloride and several types of alkyl chlorides with metal silicon]

| | | | | | | Compositions of Reaction Products (%) | | | |
|---|---|---|---|---|---|---|---|---|---|
| Exam. Nos. | RCls | Molar ratio of $CH_2Cl_2$ | $CH_2Cl_2$ (g) | Reaction Time (hr) | Product (g) | Compound of formula (III) | Compound of formula (IV) | Compound of formula (V) | Balance |
| 6-1 | t-BuCl | 1:3 | 106.0 | 4.0 | 158.8 | 15.4 | 27.1 | 10.8 | 46.7 |
| 6-2 | t-BuCl | 1:3 | 106.0 | 4.0 | 182.6 | 13.2 | 20.6 | 8.3 | 57.9 |
| 6-3 | i-PrCl | 1:3 | 106.0 | 4.0 | 156.3 | 14.5 | 26.2 | 11.4 | 47.9 |

EXAMPLES 7-1 to 7-3

Reactions of a gaseous mixture of methylene chloride and alkyl chloride or hydrogen chloride with metal silicon using a fluidized-bed reactor 402 g of the contact mixture of Sample No. I-3 of Table 1 was added into a fluidized-bed reactor and in turn heated to a temperature of 320° C. Thereafter, a mixture of 1:3 mixing ratio of start materials, that is, silane and t-butyl chloride, said t-butyl chloride being used as a source of hydrogen chloride, was added into the reactor through a preheated pipe mounted on a lower part of the reactor. In this case, dried nitrogen gas was added to the mixed start materials at a rate of 250 ml/min in order to promote the fluidization of the contact mixture. When 2 hours of reaction time elapsed, 106.0 g of methylene chloride had been used while 108.7 g of reaction product had been prepared. Table 6 shows the results of the reactions which were carried out under the condition of the same fluidized-bed reactor, the same reaction temperature and the same contact mixture with change of the source of hydrogen chloride. Particularly, the reactions of Examples 7-2 and 7-3 were carried out under the same condition except for the reaction pressure. Otherwise stated, the reaction of Example 7-3 was carried out at a reaction pressure of 3.0 kg/cm.

2H, $-CH_2$), 1.45–1.38 (m, 2H, $-CH_2-$)] and 13.1 g (11.6%) of 1,1,1,4,4,4-hexachloro-1,4-disilabutane (V) [boiling point: 204°–206° C.; NMR (δ, CDCl₃) 1.58 (s, 4H, $-CH_2-$)]. In addition, 10.4% of 1,2-dichloroethane, the start material, was recovered along with preparation of side products, such as trichlorosilane and tetrachlorosilane.

EXAMPLE 9

Reaction of a gaseous mixture of 1,3-dichloropropane and hydrogen chloride with metal silicon 95.2 g of 1,3-dichloropropane was reacted with metal silicon under the same condition as that of Example 8 except for the reaction temperature, otherwise stated, substituting the reaction temperature 280° C. for the reaction temperature 320° C., for 2 hours and, as a result, 59.2 g of reaction product was prepared. In accordance with fractional distillation of the reaction product, the composition of the reaction product was determined to be 3.5 g (5.8%) of 1,1,5,5-tetrachloro-1,5-disilapentane (III) [boiling point: 198°–200° C.; NMR (δ, CDCl₃) 5.55 (t, 2H, Si—H), 1.89–1.78(m, 2H, $-CH_2-$), 1.38–1.32 (m, 4H, $-CH_2$)], 1.8 g (3.1%) of 1,1,1,5,5-pentachloro-1,5-disilapentane (IV) [boiling point: 213°–215° C.; NMR (δ, CDCl₃) 5.56(t, 1H, Si—H), 1.95–1.82(m, 2H, $-CH_2-$), 1.59(m, 2H, $-CH_2-$), 1.41–1.33(m, 2H, $-CH_2$)] and 0.6 g (1.0%) of 1,1,1,5,5,5-hexachloro-1,5-disilapentane (V) [boiling point: 230°–232° C.; NMR (δ, CDCl₃) 2.00–1.87(m, 2H, $-CH_2-$), 1.63–1.56 (m, 4H, $-CH_2-$)]. In addition, 5.4% of 1,3-dichloropropane, the start material, was

TABLE 6

[Results of reactions of gaseous mixture of methylene chloride and alkyl chloride or hydrogen chloride with metal silicon using a fluidized-bed reactor]

| | | | | | | Compositions of Reation Products (%) | | | | | |
|---|---|---|---|---|---|---|---|---|---|---|---|
| Exam. Nos. | R'—Cl (R') | Molar ratio of $CH_2Cl_2$ | $CH_2Cl_2$ (g) | Reaction Time (hr) | Product (g) | Compound of formula (III) | Compound of formula (IV) | Compound of formula (V) | Balance | Recovered $CH_2Cl_2$ | Others |
| 7-1 | t-Bu | 1:3 | 106.0 | 2.0 | 108.7 | 10.6 | 22.4 | 8.6 | 43.0 | 15.4 | |
| 7-2 | H | 1:3 | 106.0 | 2.0 | 105.7 | 9.7 | 24.6 | 10.2 | 39.2 | 16.2 | |
| 7-3 | H | 1:3 | 106.0 | 2.0 | 121.6 | 14.3 | 28.2 | 9.5 | 40.2 | 7.8 | 3.0 kg/cm² |

EXAMPLE 8

Reaction of a gaseous mixture of 1,2-dichloroethane and hydrogen chloride with metal silicon 100.5 g of 1,2-dichloroethane was reacted with metal silicon under the same condition as that of Example 3-4 for 2 hours and, as a result, 112.7 g of reaction product was prepared. In accordance with fractional distillation of the reaction product, the composition of the reaction product was determined to be 1.0 g (0.9%) of 1,1,4,4-tetrachloro-1,4-disilabutane (III) [boiling point: 171°–172° C.; NMR (δ, CDCl₃) 5.56 (t, 2H, Si—H), 1.32 (d, 4H, $-CH_2-$)], 11.3 g (10.0%) of 1,1,1,4,4-pentachloro-1,4-disilabutane (III) [boiling point: 186°–187° C.; NMR (δ, CDCl₃) 5.58 (t, 1H, Si—H), 1.57–1.50 (m, recovered along with preparation of side products, such as trichlorosilane and tetrachlorosilane.

EXAMPLE 10

Reaction of a gaseous mixture of 1,4-dichlorobutane and hydrogen chloride with metal silicon A mixture of 1:3 mixing ratio of 1,4-dichlorobutane and hydrogen chloride was reacted with metal silicon under the same condition as that of Example 9 for 2 hours. When 2 hours of the reaction time elapsed, 92.8 g of 1,4-dichlorobutane had been used while 125.6 g of reaction product had been prepared. In accordance with fractional distillation of the reaction product, the composition of the reaction product was determined to be 15.6 g (12.3%) of 1,1,6,6-tetrachloro-1,6-disilahexane (III) [boiling point: 222°-224° C.; NMR (δ, CDCl₃) 5.54(t, 2H, Si—H), 1.66(m, 4H, —CH₂—), 1.25(m, 4H, —CH₂—)], 13.1 g (10.5%) of 1,1,1,6,6-pentachloro-1,6-disilahexane (IV) [boiling point: 240°-242° C.; NMR (δ, CDCl₃) 5.54(t, 1H, Si—H), 1.69(m, 4H, —CH₂—), 1.45(m, 2H, —CH₂—), 1.26(m, 2H, —CH₂)] and 9.0 g (7.2%) of 1,1,1,6,6,6-hexachloro-1,6-disilahexane (V) [boiling point: 255°-257° C.; NMR (δ, CDCl₃) 1.70(m, 4H, —CH₂), 1.46(m, 4H, —CH₂)]. In addition, 7.2% of 1,4-dichlorobutane, the start material, was recovered along with preparation of side products, such as trichlorosilane and tetrachlorosilane.

EXAMPLE 11

Reaction of a gaseous mixture of α,α-dichlorotoluene and hydrogen chloride with metal silicon A mixture of 1:3 mixing ratio of α,α-dichlorotoluene and hydrogen chloride was reacted with metal silicon under the same condition as that of Example 9 for 2 hours. When 2 hours of the reaction time elapsed, 100.3 g of α,α-dichlorotoluene had been used while 116.0 g of reaction product had been prepared. In accordance with fractional distillation of the reaction product, the composition of the reaction product was determined to be 14.2 g (12.2%) of 1,1,3,3-tetrachloro-2-phenyl-1,3-disilapropane (III) [boiling point: 133°-134° C./20 torr; NMR (δ, CDCl₃) 7.26-7.21(m, 5H, Ph), 5.70(d, 2H, Si—H), 2.78(t, 1H, —CH=)], 12.3 g (10.6%) of 1,1,1,3,3-pentachloro-2-phenyl-1,3-disilapropane (IV) [boiling point: 142°-144° C./20 torr; NMR (δ, CDCl₃) 7.30-7.25(m, 5H, Ph), 5.77(d, 1H, Si—H), 3.00(t, 1H, —CH=)] and 8.7 g (7.5%) of 1,1,1,3,3,3-hexachloro-2-phenyl-1,3-disilapropane (V) [boiling point: 150°-152° C./20 torr; NMR (δ, CDCl₃) 7.30-7.25(m, 5H, Ph), 3.22(s, 1H, —CH=)]. In addition, side products, that is, trichlorosilane and tetrachlorosilane, were prepared along with 4.5% of benzyldichlorosilane and 1.3% of benzyltrichlorosilane.

The present invention has been described in detail with particular reference to preferred embodiments thereof, but it will be understood that variations and modifications can be effected within the spirit and scope of the accompanying claims.

What is claimed is:

1. A bis(silyl)alkane represented by the formula (III)

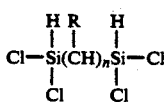
(III)

wherein R is a hydrogen atom and n is an integer ranging from 2 to 4 or R is a phenyl and n is 1.

2. A bis(silyl)alkane represented by the formula (IV)

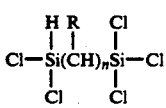
(IV)

wherein R is a phenyl and n is 1.

3. A bis(silyl)alkane represented by the formula (V)

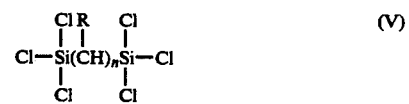
(V)

wherein R is a phenyl and n is 1.

4. A method for preparation of bis(silyl)alkanes represented by the formulas (III), (IV) and (V) comprising the steps of:

mixing an organic compound, which is represented by the formula (I) and has a chloro at each side of its molecule, with a hydrogen chloride or an organic chloride represented by the formula (II), said organic chloride being capable of generating said hydrogen chloride during its reaction, in order to provide a mixture; and directly reacting said mixture with a metal silicon at a reaction temperature of 260° C.-370° C. in the presence of a copper catalyst

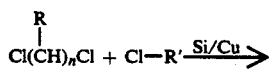

(I)    (II)

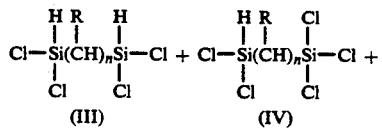

(III)    (IV)

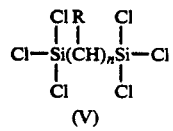

(V)

wherein R is a hydrogen atom or a phenyl, R' is a hydrogen atom or C₁₋₄ alkyl and n is an integer ranging from 1 to 4.

5. A method according to claim 4, wherein in said compound represented by the formula (I), R is a hydrogen atom and n is 1.

6. A method according to claim 4, wherein in said compound represented by the formula (I), R is a phenyl and n is 1.

7. A method according to claim 4, wherein in said compound represented by the formula (II), R' is a hydrogen atom.

8. A method according to claim 4, wherein in said compound represented by the formula (II), R' is a n-propyl.

9. A method according to claim 4, wherein in said compound represented by the formula (II), R' is a n-butyl.

10. A method according to claim 4, wherein in said compound represented by the formula (II), R' is a t-butyl.

11. A method according to claim 4, wherein said mixture has a molar ratio of 1-3:1 of said organic chloride or hydrogen chloride represented by the formula (II) and said silane compound represented by the formula (I).

12. A method according to claim 4, wherein the reaction is carried out using a fluidized-bed reactor or an agitation reactor having a spiral agitator.

13. A method according to claim 4, wherein the reaction is carried out at 1-5 atm.

14. A method according to claim 4, wherein spherical micro powder of acid white clay of 1-50% by weight of said metal silicon is additionally added to the reactants in order to improve fluidity of said reactants.

15. A method according to claim 4, wherein a copper or a copper compound, said copper compound being capable of generating the copper under the reaction condition, of 1-20% by weight of the reactants is added to said reactants as a catalyst.

16. A method according to claim 4, wherein a cocatalyst of 0.01-5% by weight of solid reactants is added to the reactants, said cocatalyst comprising at least one of the metals calcium, zinc, lead, cadmium, manganese, magnesium, silver and chrome, and compounds thereof.

* * * * *